(12) United States Patent
Deno et al.

(10) Patent No.: US 7,292,888 B2
(45) Date of Patent: Nov. 6, 2007

(54) CARDIAC STIMULATION DURING A REFRACTORY PERIOD

(75) Inventors: D. Curtis Deno, Andover, MN (US); David E. Euler, Maple Grove, MN (US); Lawrence J. Mulligan, Andover, MN (US); Edwin G. Duffin, North Oaks, MN (US); David A. Igel, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 606 days.

(21) Appl. No.: 10/638,855

(22) Filed: Aug. 11, 2003

(65) Prior Publication Data

US 2005/0038479 A1    Feb. 17, 2005

(51) Int. Cl.
*A61N 1/365* (2006.01)
(52) U.S. Cl. .............................. 607/17; 607/9
(58) Field of Classification Search ...................... None
See application file for complete search history.

(56) References Cited

U.S. PATENT DOCUMENTS

| | | |
|---|---|---|
| 4,554,922 A | 11/1985 | Prystowsky et al. |
| 5,213,098 A | 5/1993 | Bennett et al. |
| 5,224,476 A | 7/1993 | Ideker et al. |
| 5,334,221 A | 8/1994 | Bardy |
| 5,356,425 A | 10/1994 | Bardy et al. |
| 5,507,784 A * | 4/1996 | Hill et al. ...................... 607/14 |
| 5,564,434 A | 10/1996 | Halperin et al. |
| 5,755,761 A | 5/1998 | Obino |
| 5,873,896 A | 2/1999 | Ideker |
| 6,115,628 A | 9/2000 | Stadler et al. |
| 6,122,553 A | 9/2000 | Ideker et al. |
| 6,128,528 A | 10/2000 | Ericksen et al. |
| 6,205,357 B1 | 3/2001 | Ideker et al. |
| 6,223,072 B1 | 4/2001 | Mika et al. |

(Continued)

FOREIGN PATENT DOCUMENTS

WO    WO97/25098    7/1997

(Continued)

OTHER PUBLICATIONS

Hunt et al. "ACC/AHA Guidline for the Evaluation and Management of Chronic Heart Failure in the Adult: Executive Summary", *J Am Coll Cardiol.* 2001;38(7) pp. 2101-2113.

*Primary Examiner*—Kristen Mullen
(74) *Attorney, Agent, or Firm*—Paul H. McDowall; Girma Wolde-Michael (57) ABSTRACT

A medical device, e.g., an implantable medical device, delivers one or more neurally-excitable stimulation pulses to myocardial tissue during a period when the tissue is refractory. The width of the pulses is less than or equal to approximately one half millisecond. In some embodiments, the current amplitude of the pulses is less than or equal to approximately twenty milliamps. In exemplary embodiments, the medical device delivers a pulse train of six or fewer pulses separated from each other by an interval that is greater than or equal to approximately ten milliseconds. In some embodiments, the medical device delivers pulses according to a schedule stored in a memory, or as a function of a monitored physiological parameter of a patient, such as an intracardiac pressure. In some embodiments, the medical device suspends or withholds delivery of neurally-excitable based on detection of cardiac ischemia.

22 Claims, 5 Drawing Sheets

U.S. PATENT DOCUMENTS

| | | |
|---|---|---|
| 6,233,484 B1 | 5/2001 | Ben-Haim et al. |
| 6,236,887 B1 | 5/2001 | Ben-Haim et al. |
| 6,243,603 B1 | 6/2001 | Ideker et al. |
| 6,253,108 B1 | 6/2001 | Rosborough et al. |
| 6,256,535 B1 | 7/2001 | Province et al. |
| 6,263,242 B1 | 7/2001 | Mika et al. |
| 6,317,631 B1 | 11/2001 | Ben-Haim et al. |
| 6,370,430 B1 | 4/2002 | Mika et al. |
| 6,438,408 B1 | 8/2002 | Mulligan et al. |
| 6,560,489 B2 | 5/2003 | Hauck |
| 2001/0031994 A1 | 10/2001 | Mika et al. |
| 2002/0010492 A1 | 1/2002 | Donovan et al. |
| 2003/0028221 A1 | 2/2003 | Zhu et al. |

FOREIGN PATENT DOCUMENTS

| | | |
|---|---|---|
| WO | WO98/10828 | 3/1998 |
| WO | WO98/10829 | 3/1998 |
| WO | WO98/10830 | 3/1998 |
| WO | WO98/10831 | 3/1998 |
| WO | WO98/10832 | 3/1998 |

* cited by examiner

CARDIAC STIMULATION DURING A REFRACTORY PERIOD

TECHNICAL FIELD

1. Field of the Invention

The invention relates to cardiac pacing and, more particularly, to delivery of neurally-excitable stimulation to cardiac nerves that are adjacent to or embedded in the myocardium.

2. Background

The term "heart failure" (HF) as used herein embraces congestive heart failure and/or chronic heart failure as defined by the American College of Cardiology and the American Heart Association as set forth in a report of the American College of Cardiology/American Heart Association Task Force on Practice Guidelines (Committee to revise the 1995 Guidelines for the Evaluation and Management of Heart Failure) authored by Hunt et al. (ACC/AHA guidelines for the evaluation and management of chronic heart failure in the adult: executive summary, *J Am Coll Cardiol* 2001; 38(7):2101-2113). Broadly, heart failure (HF) is a syndrome in which the heart is unable to pump an adequate supply of blood to the rest of the body.

Neurally-excitable stimulation is stimulation that, when delivered to myocardial tissue, excites the cardiac nerves but does not trigger electrical depolarization of the surrounding myocardial tissue, and, consequently, does not trigger a mechanical contraction of the heart. For this reason, neurally-excitable stimulation is sometimes referred to as non-excitatory stimulation. The stimulus does not trigger a mechanical contraction because it is too weak, i.e., below the stimulation threshold, or because it is delivered to the myocardial tissue during a period when the tissue is refractory. When myocardial tissue is in its absolute refractory state, no amount of electrical stimulation energy will trigger depolarization.

It has been suggested that delivery of neurally-excitable stimulation to myocardial tissue during the refractory period of the tissue increases the contractility, i.e., the strength of contraction, of the tissue. Increased contractility of the ventricles can cause the ventricles to generate higher pressures and, consequently, eject more blood with each contraction. Consequently, neurally-excitable stimulation has been proposed as a treatment for, among other things, heart failure.

Proposed neurally-excitable stimulation waveforms include pulses with widths and amplitudes that are significantly greater than pacing pulses, and which therefore shorten the longevity an implantable medical device, requiring device explant and replacement after an undesirably short period of time. The proposed high-energy neurally-excitable pulses can also cause the patients to whose hearts they are delivered to feel pain.

SUMMARY

In general, the invention is directed to a medical device that delivers neurally-excitable stimulation to myocardial tissue. The medical device delivers one or more neurally-excitable stimulation pulses to the myocardial tissue during periods when the tissue is refractory. In some embodiments, the medical device delivers the pulses during a period from approximately forty to eighty milliseconds after a depolarization of the tissue. In exemplary embodiments, the medical device takes the form of an implantable medical device.

In general, the energy level of neurally-excitable stimulation pulses delivered by a medical device according to the invention is similar to that of pacing pulses. Consequently, such pulses are unlikely to cause pain or undesirably shorten the life of an implantable medical device battery. The width of the pulses is less than or equal to approximately one half millisecond. In some embodiments, the current amplitude of the pulses is less than or equal to approximately twenty milliamps. In exemplary embodiments, the medical device delivers a pulse train of six or fewer pulses separated from each other by an interval that is greater than or equal to approximately ten milliseconds. Further, in exemplary embodiments, the pulses are delivered to one or more sites on either the left ventricle, right ventricle, or both ventricles of the heart. In some embodiments, the pulses are applied to the atria as well in order to enhance atrial contractility.

In some embodiments, the medical device includes a sensor that detects a physiological parameter of a patient, such as an intracardiac pressure or acceleration, and delivers neurally-excitable stimulation pulses as a function of the physiological parameter. In other embodiments, the medical device delivers stimulation pulses according to a schedule stored in a memory, e.g., during certain periods of the day. Alternatively, the medical device delivers stimulation pulses every $n^{th}$ cardiac cycle, where n is an integer greater than or equal to one, or for m consecutive cardiac cycles every $n^{th}$ cardiac cycle, where m is an integer greater than or equal to one and n is an integer greater than m.

The medical device may be capable of detecting the occurrence of episodes of cardiac ischemia by monitoring, for example, QT intervals and/or morphologies, or ST segment changes, within an electrogram signal. In such embodiments, the medical device suspends or withholds delivery of neurally-excitable stimulation pulses based on detection of cardiac ischemia.

In one embodiment, the invention is directed to a method in which a stimulation pulse is delivered to myocardial tissue of a patient during a period when the tissue is refractory. A width of the pulse is less than or equal to approximately one half millisecond, and a current amplitude of the pulse is less than or equal to approximately twenty milliamps.

In another embodiment, the invention is directed to a medical device comprising an electrode implantable within a patient, a pulse generator to delivery a stimulation pulse to myocardial tissue of a patient via the electrode, and a processor to control the pulse generator to deliver the stimulation pulse during a period when the tissue is refractory. A width of the pulse is less than or equal to approximately one half millisecond, and a current amplitude of the pulse is less than or equal to approximately twenty milliamps.

In another embodiment, the invention is directed to a computer-readable medium containing instructions. The instructions cause a programmable processor to control delivery of a stimulation pulse to myocardial tissue of a patient via the electrode during a period when the tissue is refractory. A width of the pulse is less than or equal to approximately one half millisecond, and a current amplitude of the pulse is less than or equal to approximately twenty milliamps.

In another embodiment, the invention is directed to a medical device comprising means for delivering a stimulation pulse to myocardial tissue of a patient via the electrode, and means for controlling the delivery means to delivery the stimulation pulse during a period in which the tissue is refractory. A width of the pulse is less than or equal to approximately one half millisecond, and a current amplitude of the pulse is less than or equal to approximately twenty milliamps.

In another embodiment, the invention is directed to a method in which a stimulation pulse train is delivered to myocardial tissue of a patient when the myocardial tissue is refractory. A width of each pulse of the stimulation pulse train is less than or equal to approximately one half millisecond, and adjacent pulses of the stimulation pulse train are separated by at least approximately ten milliseconds.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
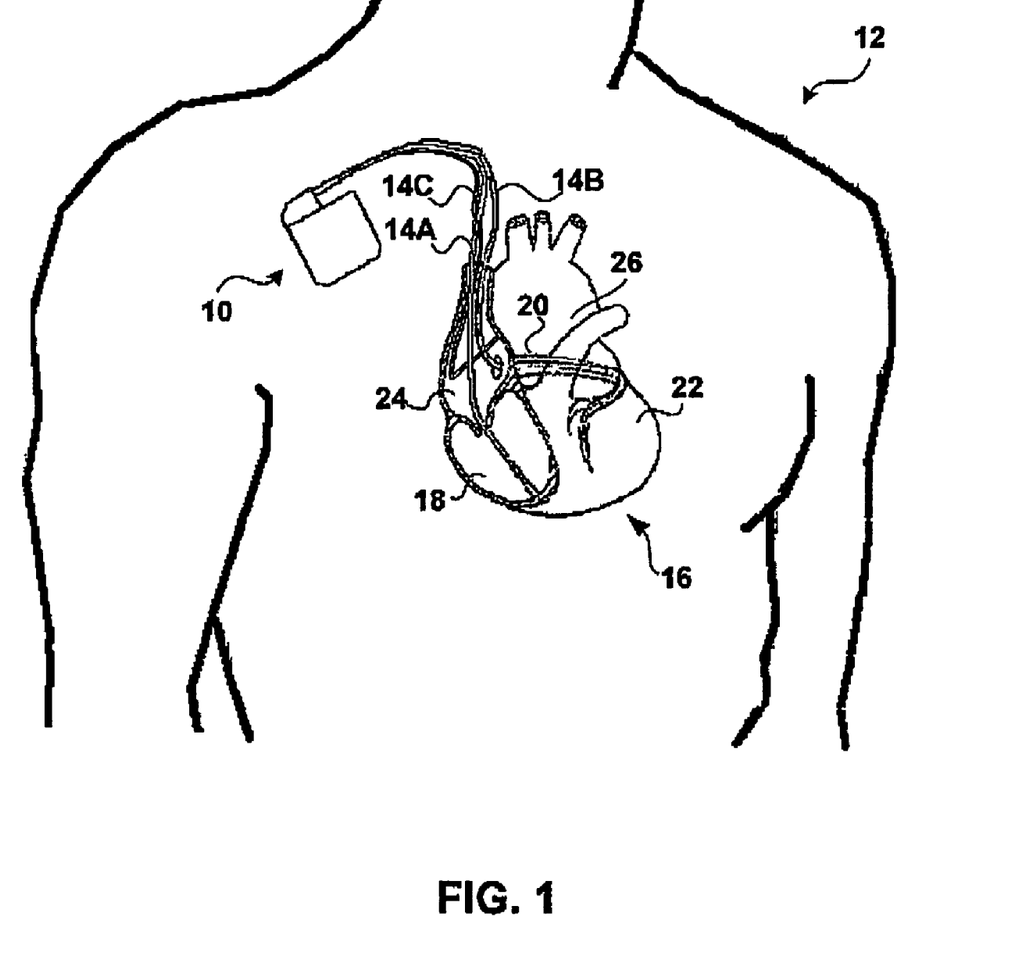
FIG. 1 is a conceptual diagram illustrating an exemplary implantable medical device that delivers neurally-excitable stimulation pulses according to the invention implanted in a patient.

FIG. 1 is a conceptual diagram illustrating an exemplary implantable medical device (IMD) 10 that delivers neurally-excitable stimulation (NES) pulses to myocardial tissue according to the invention. In some embodiments, IMD 10 takes the form of a multi-chamber cardiac pacemaker. In the exemplary embodiment illustrated in FIG. 1, IMD 10 is implanted in a patient 12, and is coupled to leads 14A, 14B and 14C (collectively "leads 14") that extend into the heart 16 of patient 12.

More particularly, right ventricular (RV) lead 14A extends through one or more veins (not shown), the superior vena cava (not shown), and right atrium 24, and into right ventricle 18. Left ventricular (LV) coronary sinus lead 14B extends through the veins, the vena cava, right atrium 24, and into the coronary sinus 20 to a point adjacent to the free wall of left ventricle 22 of heart 16. Right atrial (RA) lead 14C extends through the veins and vena cava, and into the right atrium 24 of heart 16.

Each of leads 14 includes electrodes (not shown), which IMD 10 uses to sense electrical signals attendant to the depolarization and repolarization of heart 16. IMD 10 delivers NES pulses to tissue of heart 16 at one or more locations via the electrodes located on one or more of leads 14. In some embodiments, IMD 10 also uses the electrodes located on one or more of leads 14 to deliver pacing pulses to heart 16, i.e., delivers pulses intended to cause a depolarization and contraction of heart 16. For example, the illustrated multi-chamber IMD 10 can deliver pacing pulses to ventricles 18 and 22 via the electrodes located on leads 14A and 14B with an interventricular delay therebetween to provide cardiac resynchronization therapy (CRT) to heart 16. The electrodes located on leads 14 are unipolar or bipolar, as is well known in the art.

IMD 10 delivers one or more NES pulses to tissue of heart 16 during a period in which the tissue is refractory, e.g., when stimulation energy will not trigger tissue depolarization. In exemplary embodiments, the energy level of NES pulses delivered by IMD 10 is similar to that of pacing pulses. In such embodiments, delivery of NES pulses by IMD 10 does not significantly drain the battery (not shown) of IMD 10, and is unlikely to cause patient 12 to experience pain.

The configuration of IMD 10 and leads 14 illustrated in FIG. 1 is merely exemplary. In various embodiments, IMD 10 is coupled to any number of leads 14 that extend to a variety of positions within or outside of heart 16. For example, in some embodiments, IMD 10 is coupled to a lead 14 that extends to left atrium 26 of heart 16, or epicardial leads 14 that extend to any position on an exterior surface of heart 16. Consequently, in various embodiments, IMD 10 is capable of delivering NES pulses to myocardial tissue at any location within or outside of heart 16 via electrodes located on leads 14. Further, medical devices that deliver NES pulses according to some embodiments of the invention are not implanted in patient 12, but instead are coupled to subcutaneous leads 14 that extend through the skin of patient 12 to a variety of positions within or outside of heart 16.

Figure 2:
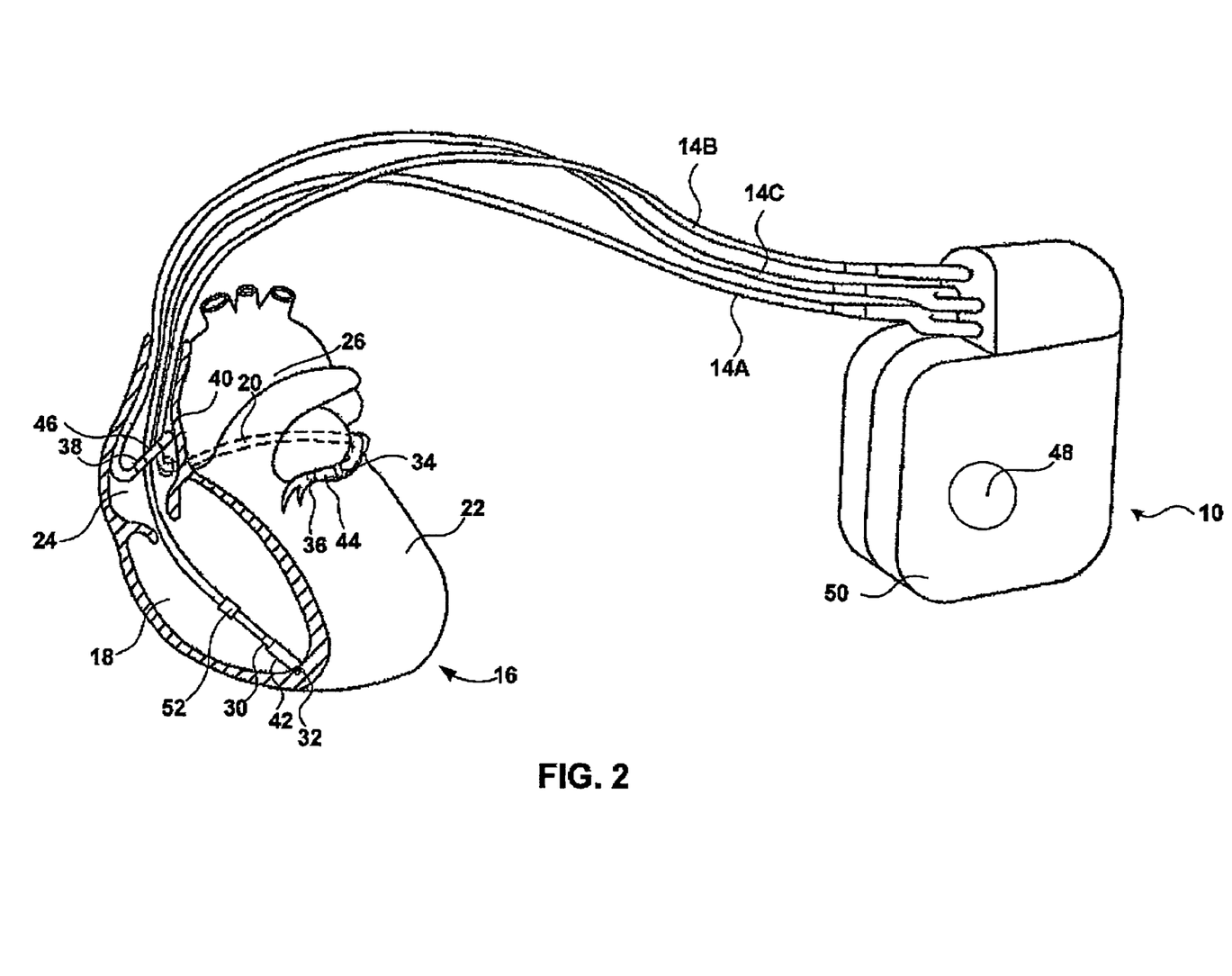
FIG. 2 is conceptual diagram further illustrating the implantable medical device of FIG. 1 and the heart of the patient.

FIG. 2 is a conceptual diagram further illustrating IMD 10 and heart 16 of patient 12. In some embodiments, each of leads 14 includes an elongated insulative lead body carrying a number of concentric coiled conductors separated from one another by tubular insulative sheaths. In the illustrated embodiment, bipolar electrodes 30 and 32, 34 and 36, and 38 and 40 are located adjacent distal end of leads 14A, 14B and 14C, respectively. In exemplary embodiments, electrodes 30, 34 and 38 may take the form of ring electrodes, and electrodes 32, 36 and 40 take the form of extendable helix tip electrodes mounted retractably within insulative electrode heads 42, 44 and 46, respectively. Each of the electrodes 30-40 is coupled to one of the coiled conductors within the lead body of its associated lead 14.

Sense/pace electrodes 30, 32, 34, 36, 38 and 40 sense electrical signals attendant to the depolarization and repolarization of heart 16. The electrical signals are conducted to IMD 10 via leads 14. In some embodiments, as described above, IMD 10 delivers pacing pulses via one or more of the bipolar electrode pairs. In the illustrated embodiment, IMD 10 also includes an indifferent housing electrode 48, formed integrally with an outer surface of the hermetically sealed housing 50 of IMD 10. In such embodiments, IMD 10 is capable of using any of electrodes 30, 32, 34, 36, 38 and 40 for unipolar sensing or pacing in combination with housing electrode 48.

IMD 10 is capable of delivering NES pulses via any combination of electrodes 30-40 and 48. In some embodiments, IMD 10 delivers defibrillation and/or cardioversion shocks to heart 16 via elongated coil defibrillation electrodes (not shown) carried on one or more of leads 14. In such embodiments, IMD is also capable of delivering NES pulses via any of electrodes 30-40 in combination with one or more of these defibrillation electrodes.

In some embodiments, IMD 10 includes a sensor 52 that generates a signal as a function of a physiological parameter of patient 12, and delivers NES pulses to tissue of heart 16 as a function of the physiological parameter. In exemplary embodiments, sensor 52 generates a signal as a function of a physiological parameter that reflects cardiac contractility, such as the derivative of an intracardiac pressure, and IMD 10 monitors the signal to identify a need for increased cardiac performance. In response to such a need, IMD 10 delivers NES pulses to increase the contractility of tissue of heart 16, which can in turn increase the cardiac output of heart 16. The most significant increase in cardiac output of heart 16 is generally achieved in embodiments where IMD 10 delivers NES pulses to tissue of one or both of ventricles 18 and 22.

In the embodiment illustrated in FIG. 2, sensor 52 is an intracardiac pressure sensor carried on lead 14A and located in right ventricle 18. In some embodiments, sensor 52 is a capacitive absolute pressure sensor, as described in U.S. Pat. No. 5,564,434 to Halperin, et al., hereby incorporated by reference herein in its entirety, a piezoelectric crystal, or piezoresistive pressure transducer. With sensor 52 located in right ventricle 18, IMD 10 is capable of estimating the pulmonary artery diastolic pressure based on the pressure in right ventricle 18 at the point of maximum positive slope in the right ventricular pressure signal generated by sensor 52. Increased pulmonary artery diastolic pressure can indicate congestion in the pulmonary vasculature, and a need for increased cardiac performance by heart 16.

The invention is not, however, limited to any particular kind of sensor 52, to any particular location of sensor 52, or any particular physiological parameter. For example, in some embodiments sensor 52 takes the form of an accelerometer located on the distal end of lead 14B to measure isovolumetric acceleration, or an oximeter located on lead 14A to measure oxygen saturation as a surrogate for flow changes. In each of these cases, the measured parameter reflects cardiac contractility. Further the invention is not limited to embodiments of IMD 10 that include a sensor that generates a signal as a function of a physiological parameter of patient 12.

Figure 3:
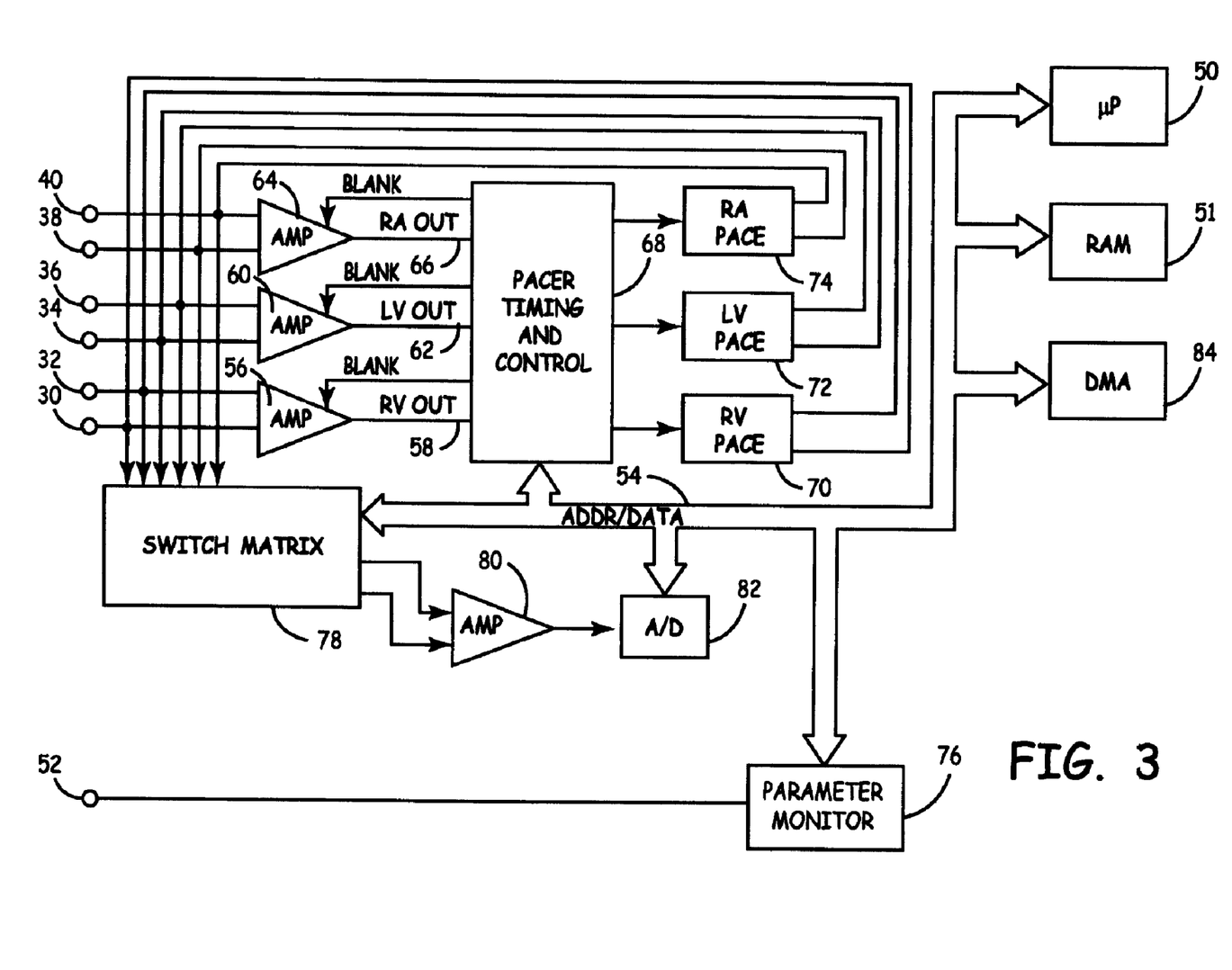
FIG. 3 is a functional block diagram of the implantable medical device of FIG. 1

FIG. 3 is a functional block diagram of IMD 10. In the illustrated embodiment, IMD 10 takes the form of a multichamber pacemaker having a microprocessor-based architecture. However, this diagram should be taken as exemplary of the type of device in which various embodiments of the present invention may be embodied, and not as limiting, as it is believed that the invention may be practiced in a wide variety of device implementations, including devices that provide NES pulses, but do not provide cardiac pacing.

IMD 10 includes a microprocessor 50. Microprocessor 50 executes program instructions stored in a memory, e.g., a computer-readable medium, such as a ROM (not shown), EEPROM (not shown), and/or RAM 51. Program instructions stored in a computer-readable medium and executed by microprocessor 50 control microprocessor 50 to perform the functions ascribed to microprocessor 50 herein. Microprocessor 50 is coupled to, e.g., to communicate with and/or control, various other components of IMD 10 via an address/data bus 54.

IMD 10 senses electrical activity within heart 16. Electrodes 30 and 32 are coupled to amplifier 56, which is an automatic gain controlled amplifier providing an adjustable sensing threshold as a function of the measured R-wave amplitude. A signal is generated on RV out line 58 whenever the signal sensed between electrodes 30 and 32 exceeds the present sensing threshold. Thus, electrodes 30 and 32 and amplifier 56 are used to detect intrinsic right ventricular depolarizations.

Electrodes 34 and 36 are coupled to amplifier 60, which also takes the form of an automatic gain controlled amplifier providing an adjustable sensing threshold as a function of measured R-wave amplitude. A signal is generated on LV out line 62 whenever the signal sensed between electrodes 34 and 36 exceeds the present sensing threshold. Thus, electrodes 34 and 36 and amplifier 60 are used to detect intrinsic left ventricular depolarizations.

Electrodes 38 and 40 are coupled to amplifier 64, which takes the form of an automatic gain controlled amplifier providing an adjustable sensing threshold as a function of the measured P-wave amplitude. A signal is generated on RA out line 66 whenever the signal between electrodes 38 and 40 exceeds the present sensing threshold. Thus, electrodes 38 and 40 and amplifier 64 are used to detect intrinsic atrial depolarizations.

IMD 10 delivers NES pulses to tissue of heart 16. Pacer timing/control circuitry 68 controls delivery of NES pulses by one or more of output circuits 70-74 via electrodes 30-40. Output circuits 70-74 include known circuitry for storage and delivery of energy in the form of pulses, such as switches, capacitors, and the like.

Pacer/timing and control circuitry 68 includes programmable digital counters that control the timing of delivery of NES pulses. Pacer/timing control circuitry 68 further controls the width and amplitude of NES pulses delivered by output circuits 70-74. Circuitry 68 controls the timing, width and amplitude of NES pulses delivered by output circuits 70-74 based on information received from microprocessor 50 via data bus 54. The timing, width and amplitude of NES pulses delivered by IMD 10 according to the invention will be described in greater detail below.

Microprocessor 50 controls the delivery of NES pulses by IMD 10 by indicating to pacer/timing control circuitry 68 when NES pulses are to be delivered, via which of electrodes 30-40 and 48 NES pulses are to be delivered, and the timing, width and amplitude of NES pulses to be delivered. In some embodiments, microprocessor 50 controls delivery of NES pulses such that NES pulses are delivered every $n^{th}$ cardiac cycle, where n is an integer greater than or equal to one. In other embodiments, microprocessor 50 controls delivery of NES pulses such that NES pulses are delivered for m consecutive cardiac cycles every $n^{th}$ cardiac cycle, where m is an integer greater than or equal to one, and n is an integer greater than or equal to m. In some embodiments, microprocessor 50 enables delivery of NES pulses according to a schedule stored in a memory, such as RAM 51, which indicates times of day or the like for delivery of NES pulses.

In some embodiments, microprocessor 50 controls delivery of NES pulses as a function of a physiological parameter of patient 12, as discussed above. A parameter monitor 76 receives the signal that is generated by sensor 52 as a function of the parameter, and processes the signal to provide values of the parameter to microprocessor 50. Where sensor 52 takes the form of an intracardiac pressure sensor, for example, parameter monitor 76 includes pressure monitoring circuitry, such as that included within the Chronicle™ Implantable Hemodynamic Monitor manufactured by and commercially available from Medtronic, Inc., to process the signal generated by sensor 52 and provide detected pressure values to microprocessor 50. Microprocessor 50 compares the values of the parameter to one or more threshold values stored in a memory, e.g., RAM 51, and directs delivery of NES pulses based on the comparison.

In some embodiments, microprocessor 50 detects ischemia of heart 16, and withholds otherwise indicated delivery of NES pulses based on the detection. In exemplary embodiments, microprocessor includes a digital signal processor (DSP), and analyzes an electrogram signal that represents electrical activity of heart 16 to detect ischemia based on changes in the QT interval length, ST segment elevation, and/or the morphology of either or both the QT interval and ST segment. Switch matrix 78 is used to select which of the available electrodes 30-40 and 48 are coupled to wide band (0.5-200 Hz) amplifier 80 for use in digital signal analysis. Selection of electrodes is controlled by microprocessor 50 via data/address bus 56, and the selections may be varied as desired.

The analog signals derived from the selected electrodes and amplified by amplifier 80 are converted to a multi-bit digital signal by A/D converter 82, and the digital signal is digitally processed by microprocessor 50 to detect, for example, elevation or depression of ST segments therein. In some embodiments, the digital signal is stored in RAM 51 under control of direct memory access circuit 84 for later analysis by microprocessor 50. In other embodiments, IMD 10 includes a separate digital processor (DSP) for analysis of the digital signal that provides an indication of ischemia to microprocessor 50. Further details regarding exemplary techniques for detecting ischemia based on an electrogram signal are found in commonly assigned U.S. Pat. Nos. 6,115,628 and 6,128,528, both to Stadler et. al., issued on Sep. 5, 2000 and Oct. 3, 2000, respectively, which are incorporated herein by reference in their entirety.

Although described herein in the context of a microprocessor-based pacemaker embodiment IMD 10, the invention may be embodied in various implantable medical devices that include one or more processors, which may be microprocessors, DSPs, FPGAs, or other digital logic circuits. Further, in some embodiments, IMD 10 does not digitally process the electrogram signal to detect ischemia. For example, IMD 10 may include analog slope or threshold detecting amplifier circuits to identify and measure the QT interval and/or ST segment within an electrogram signal, as is known in the art.

In some embodiments, IMD 10 paces heart 16. Pacer timing/control circuitry 78 includes programmable digital counters which control the basic time intervals associated with modes of pacing. Circuitry 78 also preferably controls escape intervals associated with pacing. For example, where IMD 10 paces right atrium 24, timing/control circuitry 78 triggers generation of pacing pulses by pacer output circuit 84, which is coupled to electrodes 38 and 40, upon expiration of an atrial escape interval.

IMD 10 may provide bi-ventricular pacing for cardiac resynchronization therapy. When providing bi-ventricular pacing for cardiac resynchronization therapy, pacer timing/control circuitry 68 triggers generation of pacing pulses for one of ventricles 18 and 20 by the respective one of pacer output circuits 70 and 72 upon expiration of an A-V escape interval, and the other of ventricles 18 and 20 by the respective one of pacer output circuits 70 and 72 upon expiration of a V-V escape interval.

Pacer timing/control circuitry 68 resets escape interval counters upon detection of R-waves or P-waves, or generation of pacing pulses, and thereby controls the basic timing of cardiac pacing functions. Intervals defined by pacing circuitry 68 also include refractory periods during which sensed R-waves and P-waves are ineffective to restart timing of escape intervals, and the pulse widths of the pacing pulses. The durations of these intervals are determined by microprocessor 50 in response to data stored in RAM 51, and are communicated to circuitry 68 via address/data bus 54. Pacer timing/control circuitry 68 also determines the amplitude of the cardiac pacing pulses under control of microprocessor 50.

Microprocessor 50 operates as an interrupt driven device, and is responsive to interrupts from pacer timing/control circuitry 68 corresponding to the occurrence of sensed P-waves and R-waves and corresponding to the generation of cardiac pacing pulses. Those interrupts are provided via data/address bus 56. Any necessary mathematical calculations to be performed by microprocessor 50 and any updating of the values or intervals controlled by pacer timing/control circuitry 58 take place following such interrupts.

Figure 4:
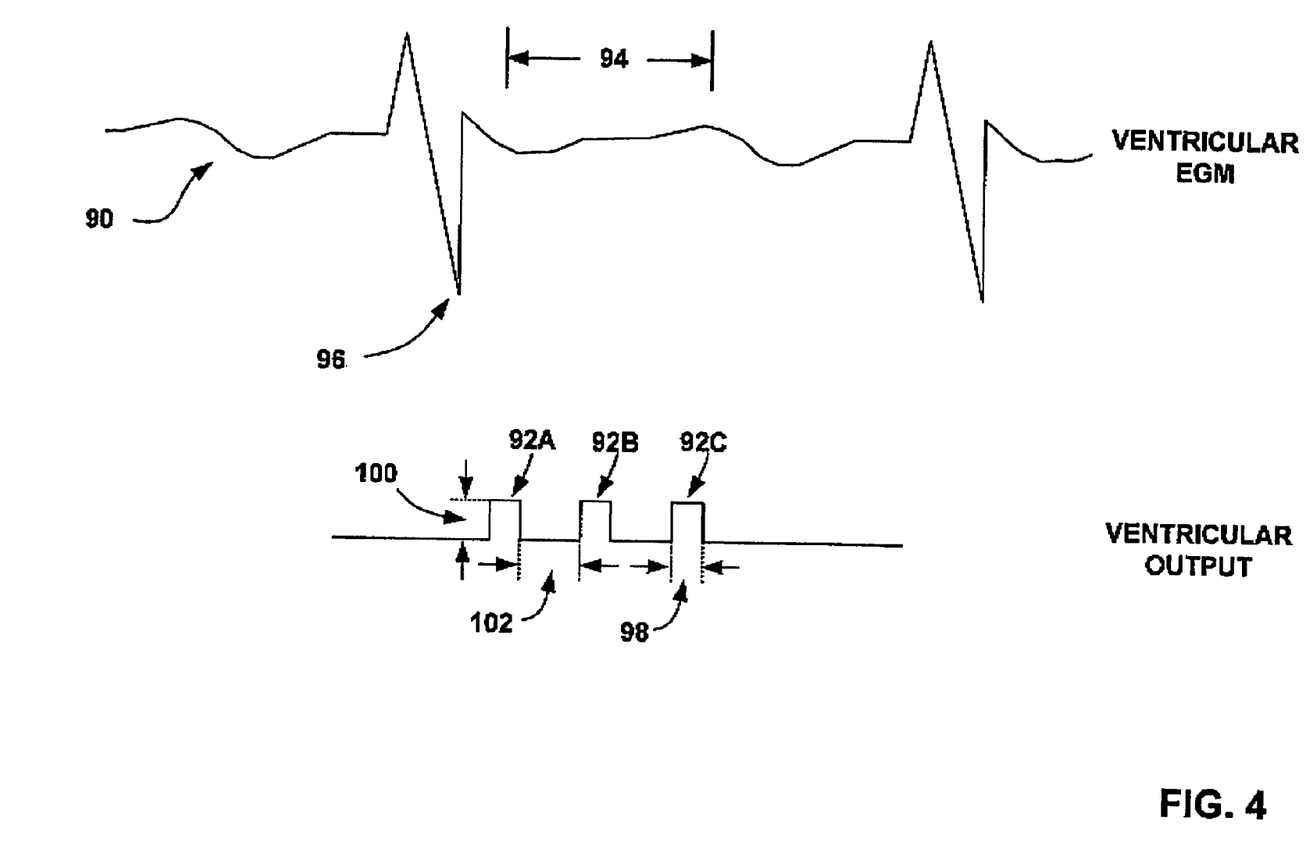
FIG. 4 is a timing diagram illustrating an example electrogram and exemplary neurally-excitable stimulation pulses.

FIG. 4 is a timing diagram illustrating an example electrogram signal 90 and exemplary NES pulses 92A-C (collectively "NES pulses 92) delivered by IMD 10 according to an embodiment of the invention. In the illustrated example, electrogram signal 90 is a ventricular electrogram signal, e.g., a signal detected via one of leads 14A and 14B. Further, as illustrated in FIG. 4, NES pulses 92 are delivered to one of ventricles 18 and 22 via one of leads 14A and 14B.

IMD 10 delivers NES pulses 92 to tissue in heart 16 during a period 94 when the tissue is refractory. When directed to control delivery of NES pulses by microprocessor 50, pacer timing/control circuitry 68 detects occurrence of an R-wave 96 in the manner described above with reference to FIG. 3, and delivers NES pulses during period 94 subsequent to R-wave 96 when tissue is refractory. In exemplary embodiments, circuitry 68 controls delivery of NES pulses during a period 94 that extends from forty to eighty milliseconds after detection of R-wave 96 to ensure that the tissue is refractory and that NES pulses 92 are delivered prior to a second depolarization of the tissue. Where NES pulses 92 are delivered to tissue of one of atria 24 and 26, refractory period 94 may be determined based on detection of a P-wave by circuitry 68 in the manner described above.

As indicated above, in exemplary embodiments the energy level of pulses 92 is similar to conventional pacing pulses. A width 98 of each of pulses 92 is less than or equal to approximately one half milliamp. Further, in some embodiments, a current amplitude 100 of each of pulses 92 is less than or equal to approximately twenty milliamps.

Although illustrated as having the same width 98 and amplitude 100, pacer timing/control circuitry 68 can deliver each of pulses 92 with different widths 98 and amplitudes 100. Further, the invention is not limited to the illustrated waveform of NES pulses 92. For example, in various embodiments, pulses 92 are biphasic or triphasic, and/or have non-square pulse shapes.

Pacer timing/control circuitry 68 controls delivery of one or more NES pulses 92 during refractory period 94. In the example illustrated in FIG. 4, circuitry 68 controls delivery of a train of three pulses 92A-C during refractory period 94. In exemplary embodiments, circuitry 68 controls delivery of pulse trains that include six of fewer NES pulses 92 during refractory period 94.

Circuitry 68 controls delivery of pulses 92 such that they are separated by an interpulse interval 102. In exemplary embodiments, interval 102 is less than or equal to ten milliseconds. Although illustrated as separated by a constant interval 102, in some embodiments, pulses 92 are separated by intervals 102 that vary from pulse-to-pulse.

Figure 5:
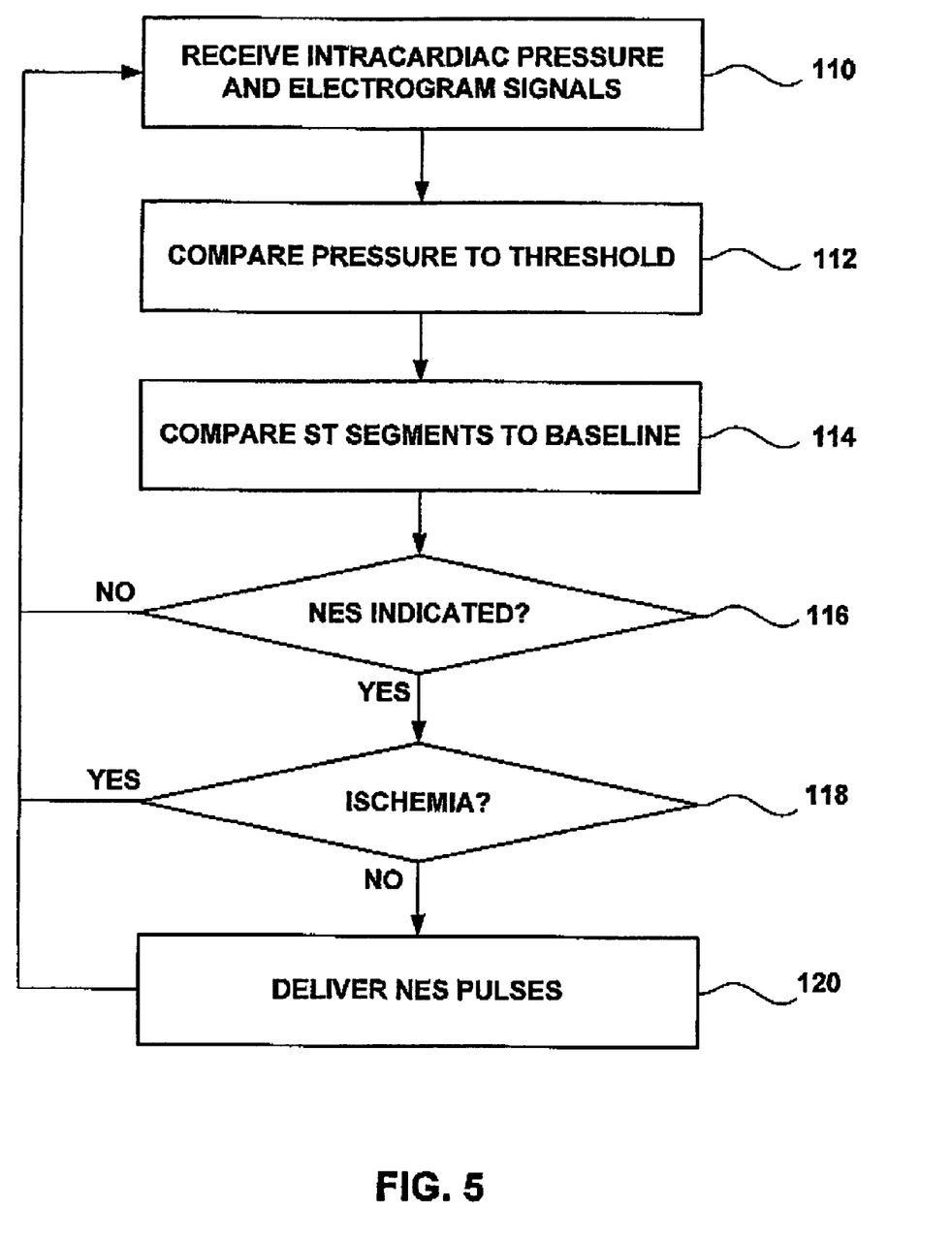
FIG. 5 is a flow diagram illustrating an example mode of operation of the implantable medical device of FIG. 1 to deliver neurally-excitable stimulation pulses.

FIG. 5 is a flow diagram illustrating an example mode of operation of IMD 10 to deliver NES pulses 92. In particular, FIG. 5 illustrates a mode in which IMD 10 delivers NES pulses 92 as a function of a monitored physiological parameter, and withholds delivery of NES pulses based on detection of ischemia.

Microprocessor 50 receives intracardiac pressure and electrogram signals (110). As described above, parameter monitor 76 receives an intracardiac pressure signal from sensor 52, and provides pressure values to microprocessor 50. Microprocessor 50 receives a digital signal from A/D converter 82 that represents an electrogram signal.

Microprocessor 50 compares the pressures received from monitor 76 to a threshold value stored in RAM 51 (112). In exemplary embodiments, the pressure values are an estimate of pulmonary artery diastolic pressure, and pressure values above the threshold value indicate a need for increased cardiac output of heart 16. Microprocessor 50 digitally processes the digital electrogram signal to compare ST segments therein to baseline values stored in RAM 51 (114).

When the pressure values exceed the threshold value, microprocessor 50 directs pacer timing/control circuitry 68 to control delivery of NES pulses 92 (116), and NES pulses 92 are delivered to myocardial tissue (120). However, if ischemia is indicated by changes in the ST segments from the baseline, microprocessor 50 withholds delivery of NES pulses 92 (118).

EXAMPLE

Experiments involving delivery of pulse trains of two to six NES pulses with widths of one half millisecond and a variety of amplitudes between one and twenty milliamps were conducted by the inventors. Pulses within a single polarity and biphasic pulses were tested using a variety of the electrode combinations discussed herein. Change in ventricular pressure over time (dP/dt) was monitored as an indicator of cardiac contractility. Significant increases in dP/dt of between approximately five and ten percent were achieved with the tested NES pulse trains.

Various embodiments of the invention have been described. However, one skilled in the art will recognize that various modifications may be made to these embodiments without departing from the scope of the invention. For example, although described herein as a treatment for heart failure, delivery of NES pulses is not limited to this use. In some embodiments, NES pulses according to the invention are delivered to treat detected electro-mechanical dissociation. In some embodiments, NES pulses are delivered acutely after open-heart surgery or delivery of defibrillation shocks.

Further, medical conditions other than those described can be used as a basis to withhold delivery of NES pulses. For example, a medical device according to some embodiments of the invention withholds delivery of NES pulses during detected episodes of tachycardia or fibrillation. In some embodiments, NES therapy is activated by a patient using a patient activator, such as a magnet activator of the type known in the art. These and other embodiments are within the scope of the following claims.

The invention claimed is:

1. A method comprising delivering a stimulation pulse to myocardial tissue of a patient during a period when the tissue is refractory, wherein a width of the pulse is less than or equal to approximately one half millisecond, and a current amplitude of the pulse is less than or equal to approximately twenty milliamps, wherein delivering a stimulation pulse comprises delivering a stimulation pulse during each of m consecutive cardiac cycles every $n^{th}$ cardiac cycle, wherein m is an integer greater than or equal to one and n is an integer greater than m.

2. The method of claim 1, wherein the period is from approximately forty to eighty milliseconds seconds after a depolarization of the myocardial tissue.

3. The method of claim 1, wherein the stimulation pulse train includes six or fewer stimulation pulses.

4. The method of claim 1, wherein delivering a stimulation pulse comprises delivering a stimulation pulse every $n^{th}$ cardiac cycle, wherein n is an integer greater than or equal to one.

5. The method of claim 1, wherein delivering a stimulation pulse comprises delivering the stimulation pulse according to a schedule stored in a memory.

6. The method of claim 1, further comprising monitoring a physiological parameter of the patient, wherein delivering a stimulation pulse comprises delivering the stimulation pulse as a function of the physiological parameter.

7. The method of claim 6, wherein the physiological parameter is indicative of cardiac output of a heart of the patient.

8. The method of claim 7, wherein monitoring a physiological parameter comprises monitoring at least one of an intracardiac pressure, an isovolumetric acceleration, and a blood oxygen saturation.

9. The method of claim 1, wherein delivering a stimulation pulse comprises delivering the stimulation pulse to a ventricle of a heart of the patient.

10. A method comprising:
   monitoring a physiological parameter of a patient wherein the physiological parameter is indicative of cardiac ischemia of a heart of the patient; and
   delivering a stimulation pulse to myocardial tissue of a patient during a period when the tissue is refractory, wherein a width of the pulse is less than or equal to approximately one half millisecond and a current amplitude of the pulse is less than or equal to approximately twenty milliamps and wherein delivering the stimulation pulse includes delivering the stimulation pulse as a function of the physiological parameter,
   wherein delivering the stimulation pulse as a function of the physiological parameter comprises:
   detecting cardiac ischemia; and
   withholding delivery of the stimulation pulse based on the detection.

11. The method of claim 10, wherein monitoring a physiological parameter comprises:
   receiving a signal that indicates electrical activity within the heart; and
   monitoring at least one of QT intervals and ST segments within the signal.

12. A medical device comprising:
   an electrode implantable within a patient;
   a pulse generator to deliver a stimulation pulse to myocardial tissue of the patient, wherein a width of the pulse is less than or equal to one half millisecond, and a current amplitude of the pulse is less than or equal to twenty milliamps;
   a processor to control the pulse generator to deliver the stimulation pulse during a period when the tissue is refractory; and
   a sensor to detect physiological parameter of the patient, wherein the processor receives a signal indicative of the physiological parameter from the sensor and controls delivery of the stimulation pulse as a function of the physiological parameter,
   wherein the sensor comprises the electrode and the signal indicates electrical activity within a heart of the patient, and
   wherein the processor detects cardiac ischemia based on the signal, and withholds delivery of the stimulation pulse based on the detection.

13. The medical device of claim 12, wherein the processor monitors at least one of a QT interval and an ST segment within the signal.

14. The medical device of claim 12, wherein the electrode is implanted within a ventricle of a heart of the patient to deliver stimulation pulses to the ventricle.

15. The medical device of claim 12, wherein the period is from forty to eighty seconds after a depolarization of the myocardial tissue.

16. The medical device of claim 12, wherein the processor controls the pulse generator to deliver a stimulation pulse train to the myocardial tissue via the electrode during the period.

17. The medical device of claim 16, wherein the stimulation pulse train includes six or fewer stimulation pulses.

18. The medical device of claim 16, wherein pulses of the stimulation pulse train are separated by at least approximately ten milliseconds.

19. The medical device of claim 12, wherein the processor controls the pulse generator to deliver a stimulation pulse every $n^{th}$ cardiac cycle, wherein n is an integer greater than or equal to one.

20. The medical device of claim 12, wherein the processor controls the pulse generator to deliver a stimulation pulse during each of m consecutive cardiac cycles every $n^{th}$ cardiac cycle, wherein m is an integer greater than or equal to one and n is an integer greater than m.

21. The medical device of claim 12, further comprising a memory to store a schedule for delivery of stimulation pulses, wherein the processor controls delivery of the stimulation pulse according to the schedule.

22. The medical device of claim 12, wherein the sensor is a pressure sensor implantable within a heart of the patient, and the physiological parameter is at least one of an intracardiac pressure, an isovolumetric acceleration, and a blood oxygen saturation.

* * * * *

UNITED STATES PATENT AND TRADEMARK OFFICE
CERTIFICATE OF CORRECTION

PATENT NO. : 7,292,888 B2  Page 1 of 1
APPLICATION NO. : 10/638855
DATED : November 6, 2007
INVENTOR(S) : Curtis Deno et al.

It is certified that error appears in the above-identified patent and that said Letters Patent is hereby corrected as shown below:

Title Pg. Item (54) Title, delete "Cardiac Stimulation During a Refractory Period" and insert in place there of --Electrically Efficient Neurally-Excitable Stimulation Technical Field--.

Signed and Sealed this

Sixth Day of January, 2009

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,292,888 B2 | |
| APPLICATION NO. | : 10/638855 | |
| DATED | : November 6, 2007 | |
| INVENTOR(S) | : Curtis Deno et al. | |

It is certified that error appears in the above-identified patent and that said Letters Patent is hereby corrected as shown below:

Title Pg. Item (54) and Column 1, lines 1 and 2, Title, delete "Cardiac Stimulation During a Refractory Period" and insert in place there of --Electrically Efficient Neurally-Excitable Stimulation Technical Field--.

This certificate supersedes the Certificate of Correction issued January 6, 2009.

Signed and Sealed this

Third Day of February, 2009

JOHN DOLL
*Acting Director of the United States Patent and Trademark Office*